(12) United States Patent
Peters

(10) Patent No.: US 9,084,978 B2
(45) Date of Patent: *Jul. 21, 2015

(54) PRODUCTION OF CHEMICAL COMPOUNDS

(76) Inventor: Bruce H. Peters, Colorado Springs, CO (US)

( * ) Notice: Subject to any disclaimer, the term of this patent is extended or adjusted under 35 U.S.C. 154(b) by 592 days.

This patent is subject to a terminal disclaimer.

(21) Appl. No.: 13/445,751

(22) Filed: Apr. 12, 2012

(65) Prior Publication Data

US 2012/0252999 A1 Oct. 4, 2012

Related U.S. Application Data

(63) Continuation-in-part of application No. 13/221,814, filed on Aug. 30, 2011, now Pat. No. 8,721,980.

(60) Provisional application No. 61/469,233, filed on Mar. 30, 2011.

(51) Int. Cl.
*B01J 19/00* (2006.01)
*B01J 10/00* (2006.01)
(Continued)

(52) U.S. Cl.
CPC ............ *B01J 10/007* (2013.01); *B01J 19/26* (2013.01); *C01B 3/382* (2013.01); *C01B 17/04* (2013.01);
(Continued)

(58) Field of Classification Search
CPC ............ C07C 1/00; C07C 1/02; C07C 1/04; C07C 1/0405; C07C 1/041; C07C 1/0415; C07C 1/0425; C07C 1/0455; C07C 2/76; C07C 2/78; C07C 9/00; C07C 9/02; C07C 9/04; B01J 8/00; B01J 8/001; B01J 8/0015; B01J 8/0065; B01J 8/02; B01J 8/08; B01J 8/18; B01J 8/12; B01J 8/1845; B01J 8/1881; B01J 8/24; B01J 8/34; B01J 19/00; B01J 19/24; B01J 19/30; B01J 19/305; B01J 35/00; B01J 35/02; F23C 1/00; F23C 13/00; F23C 13/08; F23K 5/00; F23K 5/002; F23K 5/007; F23K 5/02; F23K 5/08; F23K 5/10; F23M 2900/00; F23M 2900/05002

USPC ............ 422/129, 187, 198, 21; 423/262, 302, 423/304, 322, 387, 396, 398, 400, 421, 427, 423/445 R, 446, 448, 462, 522, 544, 549, 423/567.1, 379, 613, 636

See application file for complete search history.

(56) References Cited

U.S. PATENT DOCUMENTS

| 3,297,777 A | 1/1967 | Grantom et al. |
| 3,694,770 A | 9/1972 | Burwell et al. |

(Continued)

FOREIGN PATENT DOCUMENTS

| JP | 59038514 | 3/1984 |
| KR | 2009-071939 A | 7/2009 |

(Continued)

OTHER PUBLICATIONS

Nishida, M., "Effect of Electronic Excitiation on Laser Heating of a Stationary Plasma", 1982, J. Phys. D: Appl. Phys., 15, 1951-1954.

(Continued)

*Primary Examiner* — Natasha Young
(74) *Attorney, Agent, or Firm* — Mark D. Trenner; Trenner Law Firm

(57) ABSTRACT

Systems and methods of producing chemical compounds are disclosed. An example chemical production system includes a combustion chamber having intake ports for entry of a gas mixture. An igniter ignites the gas mixture in the intake chamber to facilitate a reaction at a high temperature and high pressure. A nozzle restricts exit of the ignited gas mixture from the combustion chamber. An expansion chamber cools the ignited gas. The expansion chamber has an exhaust where the cooled gas exits the expansion chamber. A chemical compound product is formed in the expansion chamber.

20 Claims, 3 Drawing Sheets

(51) Int. Cl.

| | |
|---|---|
| B01J 19/26 | (2006.01) |
| C01B 3/38 | (2006.01) |
| C01B 17/04 | (2006.01) |
| C01B 17/74 | (2006.01) |
| C01B 23/00 | (2006.01) |
| C01B 25/02 | (2006.01) |
| C01B 25/26 | (2006.01) |
| C01B 25/28 | (2006.01) |
| C01B 31/02 | (2006.01) |
| C01B 31/04 | (2006.01) |
| C01B 31/06 | (2006.01) |
| C01D 7/16 | (2006.01) |
| C01D 9/06 | (2006.01) |
| C01F 11/38 | (2006.01) |
| C01F 11/40 | (2006.01) |
| C01G 23/07 | (2006.01) |
| C01G 49/08 | (2006.01) |
| C07C 273/04 | (2006.01) |
| C07D 251/60 | (2006.01) |
| C08F 120/44 | (2006.01) |
| F23C 15/00 | (2006.01) |
| F23G 7/00 | (2006.01) |
| C01C 1/18 | (2006.01) |
| C07C 1/12 | (2006.01) |
| C01B 21/40 | (2006.01) |
| C01B 21/30 | (2006.01) |
| C01C 1/04 | (2006.01) |
| B01J 19/24 | (2006.01) |
| B01J 19/30 | (2006.01) |
| B01J 8/00 | (2006.01) |
| B01J 8/02 | (2006.01) |
| B01J 35/00 | (2006.01) |
| B01J 35/02 | (2006.01) |
| C07C 1/00 | (2006.01) |
| C07C 2/76 | (2006.01) |
| C07C 2/78 | (2006.01) |
| C07C 9/00 | (2006.01) |
| F23C 1/00 | (2006.01) |
| F23C 13/00 | (2006.01) |
| B82Y 40/00 | (2011.01) |

(52) U.S. Cl.
CPC ............ *C01B 17/74* (2013.01); *C01B 21/30* (2013.01); *C01B 21/40* (2013.01); *C01B 23/0005* (2013.01); *C01B 25/02* (2013.01); *C01B 25/26* (2013.01); *C01B 25/28* (2013.01); *C01B 31/02* (2013.01); *C01B 31/04* (2013.01); *C01B 31/06* (2013.01); *C01C 1/04* (2013.01); *C01C 1/18* (2013.01); *C01D 7/16* (2013.01); *C01D 9/06* (2013.01); *C01F 11/38* (2013.01); *C01F 11/40* (2013.01); *C01G 23/07* (2013.01); *C01G 49/08* (2013.01); *C07C 1/12* (2013.01); *C07C 273/04* (2013.01); *C07D 251/60* (2013.01); *C08F 120/44* (2013.01); *F23C 15/00* (2013.01); *F23G 7/00* (2013.01); *B01J 2219/00123* (2013.01); *B01J 2219/00128* (2013.01); *B82Y 40/00* (2013.01); *C01B 2203/0244* (2013.01)

(56) References Cited

U.S. PATENT DOCUMENTS

| | | |
|---|---|---|
| 4,185,559 A | 1/1980 | Little |
| 4,186,058 A | 1/1980 | Katz et al. |
| 4,294,812 A | 10/1981 | Oler |
| 4,304,308 A | 12/1981 | Munding et al. |
| 4,433,540 A | 2/1984 | Cornelius et al. |
| 4,580,504 A | 4/1986 | Beardmore et al. |
| 4,595,459 A | 6/1986 | Kusakawa et al. |
| 4,697,358 A * | 10/1987 | Kitchen ................. 34/191 |
| 4,886,444 A | 12/1989 | Hirase et al. |
| 5,188,806 A | 2/1993 | Kuehner et al. |
| 5,279,260 A | 1/1994 | Munday |
| 5,797,737 A * | 8/1998 | Le Gal et al. ........... 431/170 |
| 5,925,223 A | 7/1999 | Simpson et al. |
| 5,932,074 A | 8/1999 | Hoiss |
| 6,003,301 A | 12/1999 | Bratkovich et al. |
| 6,146,693 A | 11/2000 | Chernyshov et al. |
| 6,398,125 B1 | 6/2002 | Liu et al. |
| 6,460,342 B1 | 10/2002 | Nalim |
| 6,722,295 B2 | 4/2004 | Zauderer |
| 7,097,675 B2 | 8/2006 | Detering et al. |
| 7,225,620 B2 | 6/2007 | Klausner et al. |
| 7,241,522 B2 | 7/2007 | Moulthrop et al. |
| 7,354,561 B2 | 4/2008 | Kong |
| 8,043,479 B2 | 10/2011 | Duesel, Jr. et al. |
| 8,721,980 B2 | 5/2014 | Peters |
| 2002/0117125 A1 | 8/2002 | McMaster et al. |
| 2002/0151604 A1 | 10/2002 | Detering et al. |
| 2003/0021746 A1 | 1/2003 | Fincke et al. |
| 2004/0219400 A1 | 11/2004 | Al-Hallaj et al. |
| 2005/0097819 A1 | 5/2005 | Lomax, Jr. et al. |
| 2005/0103643 A1 | 5/2005 | Shoup |
| 2005/0109604 A1 | 5/2005 | Zlotopolski |
| 2006/0083671 A1 | 4/2006 | Obayashi et al. |
| 2007/0051611 A1 | 3/2007 | Rives et al. |
| 2007/0072027 A1 | 3/2007 | Sridhar et al. |
| 2007/0128477 A1 | 6/2007 | Calhoon |
| 2007/0193870 A1 | 8/2007 | Prueitt |
| 2008/0141974 A1 | 6/2008 | Bechtel |
| 2010/0126867 A1 | 5/2010 | Riviello |
| 2010/0154429 A1 | 6/2010 | Peters |
| 2010/0187128 A1 | 7/2010 | Neubert et al. |
| 2010/0224477 A1 | 9/2010 | Peters |
| 2011/0024283 A1 | 2/2011 | Peters |
| 2011/0047962 A1 | 3/2011 | Kenyon et al. |
| 2011/0126511 A1 | 6/2011 | Glaser et al. |
| 2011/0174605 A1 | 7/2011 | Ugolin |
| 2012/0321528 A1 | 12/2012 | Peters |
| 2013/0161007 A1 | 6/2013 | Wolfe et al. |
| 2014/0134057 A1 | 5/2014 | Peters |

FOREIGN PATENT DOCUMENTS

| | | |
|---|---|---|
| KR | 10-2007-0139882 | 11/2009 |
| WO | 94-23186 A1 | 10/1994 |

OTHER PUBLICATIONS

International Search Report and Written Opinion for PCT/US2012/052563 dated Jan. 23, 2013, 10 pp.

Machine translation of KR 2009071939 A, Application No. KR 1020070139882, which was published Jul. 2, 2009.

English Abstract of KR 2009071939 A, which was previously published as KR 1020070139882 and discloses the relationship and which was published Jul. 2, 2009.

International Search Report and Written Opinion dated Oct. 30, 2012 for PCT/US2012/033369, 10 pp.

International Search Report and Written Opinion for Int. Appl. No. PCT/US2011/049793, mailed Apr. 25, 2012, 9 pp.

Chao, R.E., "Thermochemical Water Decomposition Processes", Industrial and Engineering Chemistry Product Research Development, 1974, p. 94-101.

International Search Report and Written Opinion dated Sep. 23, 2014 for International Application No. PCT/US2014/040627, 13 pp.

* cited by examiner

PRODUCTION OF CHEMICAL COMPOUNDS

PRIORITY CLAIM

This application claims priority to U.S. Provisional Patent Application No. 61/469,233 filed Mar. 30, 2011 and titled "Device and process for underground rock fracturing and heating and nitrate and hydrocarbon formation using a hydrogen powered pulse jet" of Bruce H. Peters, and is a continuation-in-part (CIP) of U.S. patent application Ser. No. 13/221, 814, now U.S. Pat. No. 8,721,980, filed Aug. 30, 2011 and titled "Systems and methods of producing chemical compounds" of Bruce H. Peters, each of which is hereby incorporated by reference as though fully set forth herein.

BACKGROUND

Chemical production on a commercial scale is key to many industries. Many of these processes make the production of an otherwise rare product (or even non-existent in nature) less expensive, thus making it available for public use and consumption. Production of a specific chemical product may involve more than one type of process.

While chemical production processes are currently available for meeting many of the world's needs today, these processes tend to be energy intensive. That is, these processes often require large amounts of energy to produce products, increasing the cost of production as carbon-based energy continues to increase in cost. In addition, many chemical production processes produce, in addition to the desired end-product, by-products which can be toxic, hazardous, or require special handling.

DETAILED DESCRIPTION

Systems and methods are disclosed for producing chemical compounds, which can then be used directly or as components in other processes. The systems and methods also produce focused explosive force, pressure, and heat, as well as by-products which can be used for various purposes. These and other products and applications will be understood by those having ordinary skill in the art after becoming familiar with the teachings herein.

An example chemical production system includes an intake chamber having intake ports for entry of a gas mixture. An igniter ignites the gas mixture in the intake chamber. A nozzle restricts exit of the ignited gas mixture from the intake chamber. An expansion chamber cools the ignited gas with a cooling agent. The expansion chamber has an exhaust where the cooled gas exits the expansion chamber. There may also be an exit port to remove products in aqueous and/or liquid form. A chemical compound product is formed in the expansion chamber.

An example method includes: igniting a gas mixture in an intake chamber, restricting exit of the ignited gas mixture from the intake chamber to increase temperature and pressure, cooling the ignited gas in an expansion chamber, and collecting a chemical compound product from the expansion chamber.

Before continuing, it is noted that as used herein, the terms "includes" and "including" mean, but is not limited to, "includes" or "including" and "includes at least" or "including at least." The term "based on" means "based on" and "based at least in part on."

Figure 1:
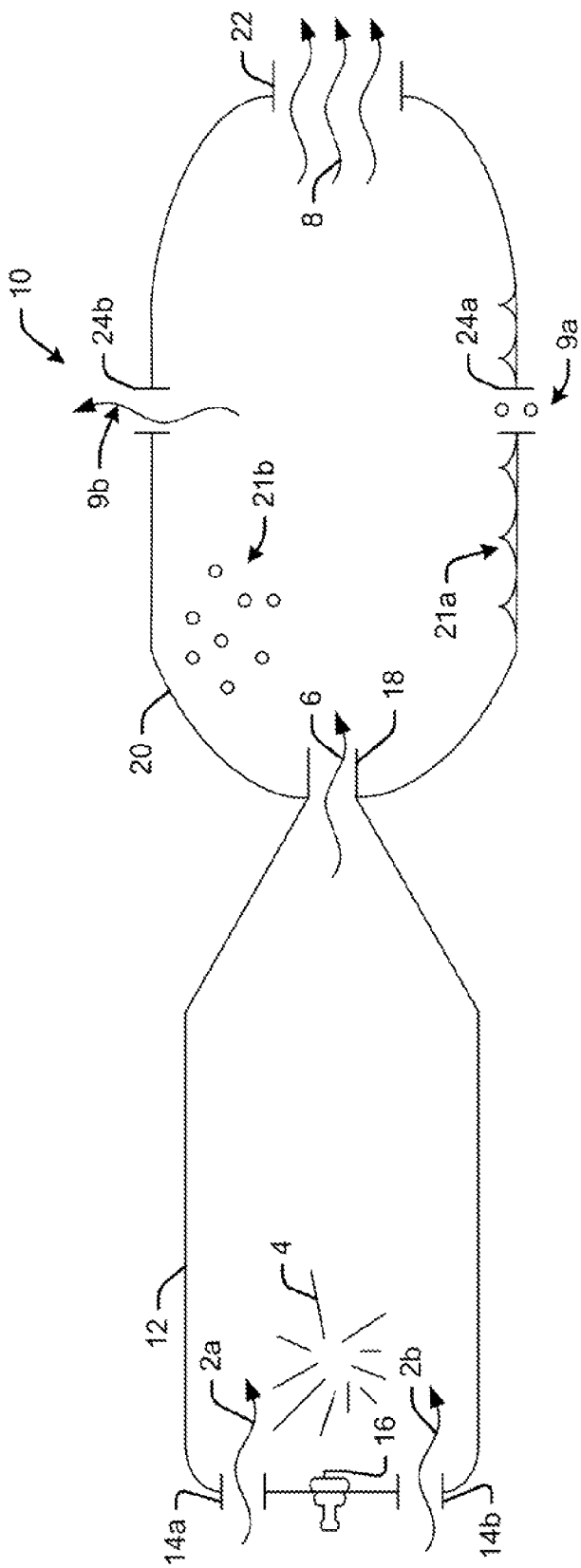
FIG. 1 shows an example chemical production system.

FIG. 1 shows an example chemical production system 10. The drawings are shown as simple schematic diagrams, but it should be appreciated that one having ordinary skill in the art will understand the construction of the system using readily available components and manufacturing techniques, based on these schematics and corresponding description herein. Other configurations of systems and devices for carrying out the operations of the chemical processes are also possible.

The example chemical production system 10 is shown in FIG. 1 including a combustion chamber or intake chamber 12. The intake chamber 12 may be configured with a number of inlet or intake ports 14*a-b* for entry of a gas mixture (illustrated by gas flow 2*a* and gas flow 2*b*).

Although two intake ports 14*a-b* are shown in a back wall of the intake chamber 12 in FIG. 1 for purposes of illustration, it is noted that any suitable number of port(s) and/or port configuration may be provided and positioned based on design considerations.

Design considerations for determining the number, sizing, and positioning of ports may include, but are not limited to, the number and type of gas or gases being introduced to the intake chamber 12, timing of the introduction of gas or gases, flow rates, pressure, and other parameters.

Figure 2:
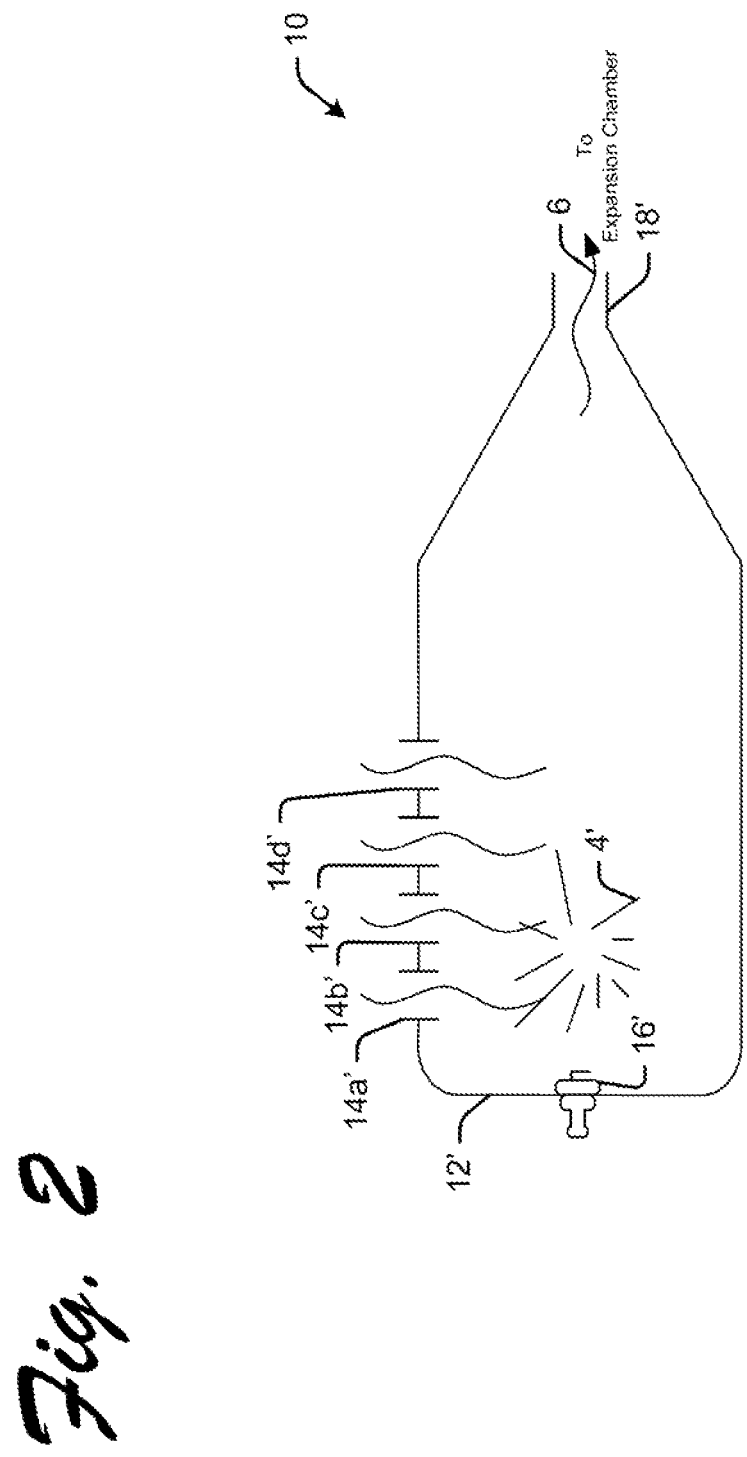
FIG. 2 shows an alternative intake chamber for the chemical production system.

For purposes of illustration, FIG. 2 shows another example intake chamber 12' having four intake ports 14*a*' through 14*d*' along an upper sidewall of the intake chamber 12'. In this example, port 14*a*' may supply hydrogen gas, port 14*b*' may supply oxygen, port 14*c*' may supply ambient air, and port 14*d*' may supply water, water vapor/steam or other gas, liquid, and/or solid directly to the intake chamber 12'. It is noted that in FIG. 1*a* the prime (') designation is used to refer to like components (as shown in FIG. 1), and may not be described separately for FIG. 2.

The process allows for a variety of products, depending on the amounts and ratio of gases combusted and the temperatures and pressures achieved, which can be further controlled by varying the amount of water vapor (which acts as a cooling and modulating agent) entering the intake chamber. In this way, chemical products are made in ratios reflecting the gases admitted to the system, and the temperature and pressures chosen.

In an example, the direct injection of water or water vapor/steam into the intake chamber 12' begins a cooling process, and absorption, before the ignited gas exits the intake chamber 12'. This configuration has been shown to favor production of chemical product at high conversion efficiencies. This configuration also results in production of liquid product. The process can be further facilitated by adding a catalyst, such as magnetite or ruthenium, or platinum, to the intake chamber 12'.

With reference again to FIG. 1, an igniter 16 is provided. The igniter 16 may be positioned to ignite the gas mixture within the intake chamber 12, as illustrated by explosion 4. The specific number and positioning of the igniter 16 may also vary based on design considerations, such as those set forth above. For example, a backup igniter may be provided.

Ignition of the gas mixture 2 causes a high temperature, high pressure explosion 4 within the intake chamber 14. Accordingly, the intake chamber 12 may be configured in such a manner so as to safely accommodate many, repeated explosions over time, without weakening the walls of the intake chamber 12. Indeed, it is found that the pressure within the chamber may be kept low for safety considerations, as the bulk of the chemical reactions occur focused within the very high temperature and pressure of the limited area of explosion within the chamber.

In an example, the intake chamber 12 tapers toward an end opposite the intake ports 14a-b. A nozzle 18 may be provided on the tapered end of the intake chamber 12. The nozzle 18 forms an outlet from the intake chamber 12, and serves as an inlet to an expansion chamber 20. A seal (not shown) may be provided between the intake chamber 12 and the expansion chamber 20. Such a configuration restricts exit of the ignited gas 6 flowing in from the intake chamber 12, thereby increasing temperature and/or pressure in the intake chamber 12 for a more efficient conversion process.

The expansion chamber 20 serves to cool the ignited gas 6 flowing into the expansion chamber 20. In an example, a cooling agent may be provided in the expansion chamber 20. The cooling agent may be water (illustrated by reference 21a), water vapor (e.g., a mist or water vapor illustrated by reference 21b), or a combination thereof. Other cooling agents may also be used and are not limited to water-based cooling agents.

The expansion chamber 20 has an exhaust 22 where the cooled gas 8 exits the expansion chamber 20. During cooling, a chemical compound product is formed in the expansion chamber 20. The chemical compound product can be collected in solid or aqueous form 9a at a collection port 24a and/or in gas form 9b at a collection port 24b. Chemical compound product is referred to generally herein by reference number 9. Again, the desired number and positioning of exhaust 22 and collection port 24 may be based at least in part on design considerations.

Figure 3:
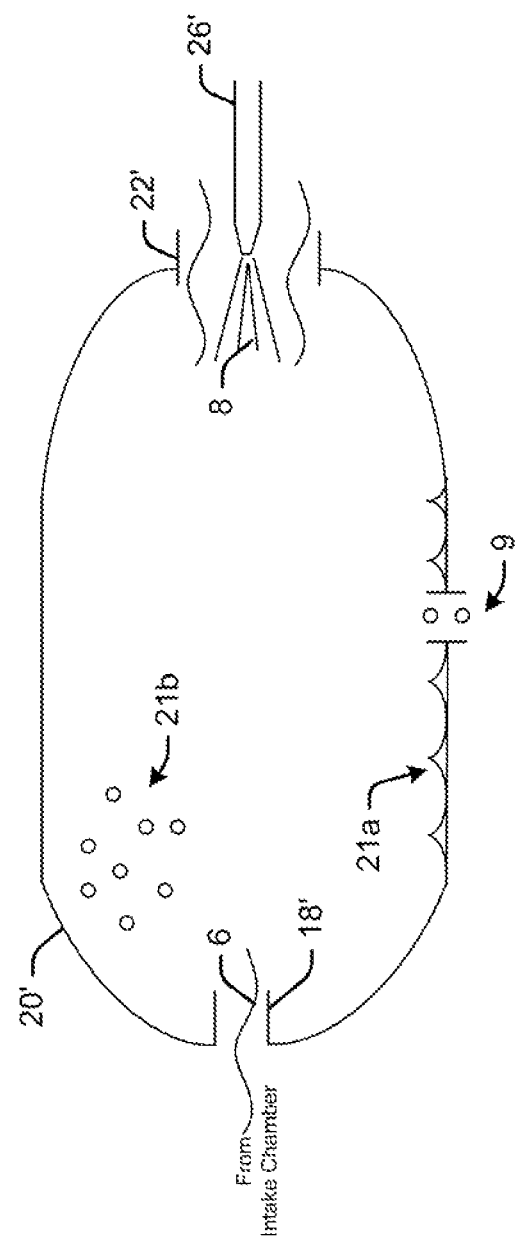
FIG. 3 shows an alternative expansion chamber for the chemical production system.

For purposes of illustration, FIG. 3 shows another example expansion chamber 20'. In this example, the expansion chamber 20' includes an injection port 26' which enables the direct injection of a supplemental cooling agent 21c into the expansion chamber 20'. For example, the injection port 26' can be used to controllably inject a fine mist or vapor of water into the expansion chamber 20'. The cooling agent 21c injected by the injection port 26 may be used as a substitute for the cooling agent already in the expansion chamber 20', or in addition to the cooling agent(s) 21a and/or 21b already provided in the expansion chamber 20'. In any event, direct injection facilitates rapid cooling of the gas 6 entering the expansion chamber 20'.

Although one injection port 26' is shown at the exhaust 22', any number and/or position of injection port(s) 26' may be provided, again based on design considerations.

It is noted that the specific materials used, and sizing of each component, may vary at least to some extent based on design considerations, desired mode of operation (see, e.g., example use cases below), and desired output product and quantity of the product. Appropriate safety precautions should also be observed due to the temperatures, pressures, and explosive nature of the reactions.

In an example, the chambers may be manufactured of stainless steel, iron, ceramic, or other materials. Nozzles, inlets, and outlets, may be manufactured of metal or other materials. Unidirectional nozzles may be utilized, and gaskets and seals may also be provided, as appropriate, in order to ensure that the proper temperature and pressures can be maintained for accomplishing the reactions.

It will be appreciated that the chemical production system 10 may be used to make any of a wide variety of chemical compounds, as described in the examples below.

Before continuing, it should be noted that the examples described above are provided for purposes of illustration, and are not intended to be limiting. In an example, the components and connections depicted in the figures may be used. Other devices and/or device configurations may also be utilized to carry out the operations described herein.

During use of the chemical production system 10, example operations may include igniting a gas mixture in an intake chamber, restricting exit of the ignited gas mixture from the intake chamber to increase temperature and pressure, cooling the ignited gas in an expansion chamber, and collecting a chemical compound product from the expansion chamber. The operations may be repeated at a rapid pace so as to be substantially continuous in nature, and/or to form a concentrated chemical compound product.

In an example, when used to produce nitrates, the reaction includes the explosion-producing chemical product in the intake chamber 12. The chemical product formed by the explosion is vented into the expansion chamber 20 containing steam or cold mist. In addition, water vapor in the ambient air (with or without using additional oxygen or nitrogen and/or with or without a catalyst) may also facilitate an environment of high heat and pressure. The temperature and pressure cause the chemical product to form nitrogen oxides, which when quickly cooled in water, forms dioxides. The dioxides can combine with the water to produce an aqueous solution. Complex compounds can be produced adiabatically.

The operations shown and described herein are provided to illustrate example implementations. It is noted that the operations are not limited to the ordering shown. Still other operations may also be implemented. It is also noted that various of the operations described herein may be automated or partially automated.

Further operations may include redirecting gas from the expansion chamber 20 to the intake chamber 12 to reduce presence of the gas in the exhaust. Further operations may also include various mechanisms for injecting the cooling agent. For example, water may be injected directly into the ignited gas 6 as the gas 6 enters the expansion chamber 20. Introducing water or other fluid may be at an angle about 180 degrees to the ignited gas 6 entering the expansion chamber 20. Still further operations may include injecting a cooling agent directly into the intake chamber 12 (e.g., as shown in FIG. 2) to begin cooling in the intake chamber 12. Beginning cooling in the intake chamber 12 has been shown to facilitate absorption and favor high-efficiency production of chemical product. Yet further operations may also include adding a catalyst to the intake chamber 12.

It is noted that the chemical production system 10 can also be used to cool gases by admitting a fluid and/or vapor. Such supplemental cooling agents can be introduced directly into the intake chamber 12 and/or the expansion chamber 20. In addition, the chemical production system 10 may be used to recover gas and/or aqueous solution. In such an example, the expansion chamber may be modified to include both a fluid collection port (for collecting liquid chemical compound product) and a gas collection port (for collecting gaseous chemical compound product). The chemical production system 10 may also be operated with multiple passes, whereby the product or by-product (e.g., gas) is reintroduced into the intake chamber. Such an example enables the chemical compound product to be concentrated and/or purified.

The chemical production system 10 may be used as a new method of performing high pressure and/or high temperature industrial chemical production with or without a catalyst in the combustion chamber. The chemical production system 10 may be used with any of a wide variety of reactants to produce different chemical products.

The chemical production system 10 may be used to make its own catalyst, which has its own commercial uses. For example, admitting H2S and SO2 and other pollutants from coal combustion are reacted to form sulfuric acid (H2SO4) and elemental sulfur (S).

By way of example, H2S and SO2 are added to the combustion chamber made of or at least partially coated with or containing lead, to produce sulfuric acid according to the following equations:

$$H_2S + 3/2 O_2 \rightarrow SO_2 + H_2O$$

$$SO_2 + 2H_2S \rightarrow 3S + 2H_2O$$

$$S + O_2 \rightarrow SO_2$$

$$NO + \tfrac{1}{2} O_2 \rightarrow NO_2$$

$$SO_2 + NO_2 \leftrightarrow SO_3 + NO$$

$$SO_3 + H_2O \rightarrow H_2SO_4$$

This may be useful for utilizing certain by-products from coal combustion, some considered pollutants, to produce a useful chemical product and cleanse a pollutant from being released into the atmosphere as from "sour" natural gas or the toxic emissions from landfills which contain $H_2S$ and/or $SO_2$, etc.

Other examples of admitting by-products and/or pollutants (e.g., CO and CO2) into the combustion chamber include production of carbon black, and other forms of carbon (e.g., C2, C4, C6, C8, graphene, and diamond).

Another use of the chemical production system 10 is for making magnetite (Fe3O4) when, in a chamber made of or containing an array of iron (Fe), the combustion is performed with an excess of oxygen so that the iron and oxygen chemically bond characteristic of the detonation/combustion of hydrogen and oxygen, which is an electro-magnetic pulse, provides the magnetization to create magnetite. Magnetite itself serves as a catalyst for the bonding of nitrogen and hydrogen to form ammonia under pressure. The iron oxide can also be made as a product and used in dyes, computerized medical imaging (e.g., CT scans), and as a catalyst for the Haber-Bosch process for ammonia production.

Other metals (e.g., vanadium and titanium) can also be oxidized by this process. In the case of magnetite, the process produces extremely small and uniform particles which are of special value. Non-metallic oxides may also be made in a similar manner.

Having described various example systems, processes, operations, and applications, reference will now be made to examples of chemical reactions which may be facilitated using the chemical production system. In each of these examples, the combustion chamber is used. It is noted that the term combustion as used herein includes explosions (e.g., detonations) and deflagration as used for gasification, and any combustion from complete combustion through incomplete combustion) Ambient air can be used to provide some or all of the oxygen and/or nitrogen for these reactions. When nitrogen is not needed, it can be withheld. But in every example discussed below, at least oxygen and hydrogen is combusted. Catalysts may also be used to augment the process. For example, the combustion chamber may be made of iron (Fe) which is converted to Fe3O4 by the combustion in excess oxygen, and serves as a catalyst for the reaction(s). Other catalysts can also be used in any of the following reactions.

It is noted that while specific parameters may be given for the following examples, all sizing, temperatures, pressures, and gas flow rates can be adjusted based on various design considerations and to achieve the desired yields. By way of example, the location of introducing precursor material and/or catalysts to the combustion chamber, pressure, and temperature may be according to a continuum of initially maximum to declining temperature and pressure as the combusted oxygen and hydrogen expand into the chamber. The specific configuration depends at least to some extent on the size and shape of the combustion chamber, as well as the amount of hydrogen and oxygen utilized. These parameters may vary for the different chemical reactions, and can be readily modeled based on known thermodynamics and adjusting variables accordingly. These parameters are provided only for the purpose of illustrating to one having ordinary skill in the art how to practice the invention, but are not intended to be limiting in any manner. It is understood that in some complex reactions, multiple products may be produced that may need to be separated by further processing.

The examples described herein are provided for purposes of illustration and are not intended to be limiting. Still other examples are also contemplated.

Example 1

In this example, $H_2SO_4$ is admitted into the combustion chamber to make ammonium sulfate according to the below equation. This occurs when a catalyst is used and the chemical production system is configured to combust without excess oxygen, thus producing $NH_3$ which reacts with the $H_2SO_4$. Admitting 1 gram of concentrated sulfuric acid in the combustion chamber along with hydrogen, ambient air, and water vapor resulted in producing 1.4 grams of ammonium sulfate.

$$2NH_3 + H_2SO_4 \rightarrow (NH_4)_2SO_4$$

Example 2

In this example, mono-ammonium phosphate and diammonium phosphate are made in the presence of ammonia admitted into the combustion chamber according to the below equation.

$$NH_3 + H_3PO_4 \rightarrow (NH_4)H_2PO_4$$

and $$2NH_3 + H_3PO_4 \rightarrow (NH_4)_2HPO_4$$

Example 3

In this example, calcium nitrate is made when $CaCO_3$ is introduced into the combustion chamber under conditions where oxygen, in excess of that consumed in the combustion, is present, thus making nitric acid. The nitric acid combines with calcium carbonate to form calcium nitrate according to the below equation. One gram of calcium in solution and in a mist was admitted into the combustion chamber along with oxygen in excess of that binding with hydrogen in combustion, and resulted in 0.5 grams of calcium nitrate.

$$CaCO_3 + 2HNO_3 \rightarrow Ca(NO_3) + CO_2 + H_2O$$

Similarly, the introduction of calcium phosphate produces calcium nitrate and phosphoric acid according to the below equation.

$$Ca_3(PO_4)_2 + 6HNO_3 + 12H_2O \rightarrow 2H_3PO_4 + 3Ca(NO_3)_2 + 12H_2O$$

If calcium hydroxide is added to the process under conditions wherein ammonium nitrate is made in a single step, calcium nitrate and ammonium hydroxide are made in a single step according to the below equation.

$$2NH_4NO_3 + CaOH_2 \rightarrow Ca(NO_3)_2 + 2NH_4OH$$

Calcium nitrate is used as fertilizer and in waste water treatment as well as an accelerant of concrete setting, and for use in cooling, such as so-called "cold packs."

Example 4

In this example, urea is made under conditions wherein the mix of combustion gases in the combustion chamber withholds excessive oxygen, thus making ammonia when carbon dioxide is also admitted (e.g., in a 3:1 molar ratio), and urea is made according to the below equation. One gram of carbon dioxide admitted to the chamber resulted in 0.45 grams of urea.

$$2NH_3 + CO_2 \rightarrow NH_2CONH_2 + H_2O$$

Example 5

In this example, sodium carbonate (soda ash) is made through the method of the Solvay process. That is, carbon dioxide is admitted into the combustion chamber when $NH_4OH$ is made according to the below equation. The reaction requires the $NH_3$ produced in the process to occur in a single step.

$$2NH_4OH + 2CO_2 \rightarrow 2NH_4HCO_3$$

and with the addition of NaCl $$2NH_4HCO_3 + 2NaCl \rightarrow 2NaHCO_3 + 2NH_4Cl$$

$$2NaHCO_3 \rightarrow Na_2CO_3 + CO_2 + H_2O$$

and then the $NH_3$ is recycled $$2NH_4Cl + Ca(OH)_2 \rightarrow 2NH_3 + CaCl_2 + 2H_2O$$

Example 6

In this example, pollutants (e.g., $H_2S$, $SO_2$, and other sulfur, potassium, hydrides, and phosphorous hydrogen containing compounds) and oxides considered pollutants and/or greenhouse gases in the emissions of coal, and also biogas, or "sour" natural gas used as an energy source in electrical power production, industrial chemical production, or in heating, are admitted to the combustion chamber. End products from the reaction include sulfuric acids and elemental sulfur as well as phosphates, and elemental phosphorous, potassium carbonate, chloride, hydroxide, nitrate, and sulfate, depending on the precursors added to the combustion chamber, or subjected to the gaseous NH3 or $NH_4OH$ produced by the combustion of $H_2$ and air (e.g., a mix of $O_2$, $N_2$, and argon gas). One gram of hydrogen sulfide admitted to the chamber produced, following combustion, a liquid testing positive for sulfur with a pH 3. The amount of the sulfuric acid produced was not determined.

Example 7

In this example, detoxification and/or combustion of organic compounds occurs in the combustion chamber, including introducing to the combustion chamber recognized toxic agents (e.g., mustard or nerve gases, and other gases designed for use in warfare), and possible organic compounds recognized as possible micro-pollutants of water (e.g., benzene, insecticides, herbicides, medication fragments, etc.).

Example 8

In this example, a carbon source (e.g., carbon monoxide and/or carbon dioxide) is introduced to the combustion chamber to produce carbon in other forms (e.g., C, $C_2$, $C_4$, $C_6$, and $C_8$, graphene, and diamond). The carbon source is subject to high pressure (e.g., up to about 500,000 bar) and heat (e.g., up to about 5500° C.) during combustion of hydrogen and oxygen with a restricted nozzle. Diamond is produced at the highest achievable temperature and pressure. Carbon is produced at a relatively low temperature. Methane and other higher molecular weight hydrocarbons are also produced during the process if hydrogen is introduced in excess of the oxygen used.

Example 9

In this example, urea ammonium nitrate is made when ammonium nitrate is combined in the combustion chamber to make urea. The two processes occur simultaneously using hydrogen powered pulse detonation/combustion in the combustion chamber.

Example 10

In this example, potassium nitrate and nitric acid is produced when hydrogen and nitrogen and potassium chloride (KCl) are introduced in the combustion chamber with excess oxygen according to the below equation:

$$2KCl + 2HNO_3 + \tfrac{1}{2}O_2 \rightarrow 2KNO_3 + H_2 + Cl_2$$

Example 11

In this example, benzene or chloro-benzene is added to the combustion chamber during production of caustic soda to produce phenols. Phenols are used to manufacture phenolic resin glues and other products.

Example 12

In this example, melamine (a plastic) is made from urea in the combustion chamber under conditions of high pressure according to the below equation.

$$6NH_2CONH_2 \rightarrow NH_2COO^-NH_4^+ \rightarrow melamine + CO_2$$

Example 13

In this example, ethylene glycol is produced when solutions of bicarbonate and ethylene chloride are added to the combustion chamber (in a stainless steel, ceramic, titanium, or other combustion chamber without $Fe_3O_4$ to prevent the production of ammonia).

Example 14

In this example, Xenon ($XeF_2$) is converted to $XeF_4$ and $XeF_8$ under high pressure and heat produced in a pulsing manner in the combustion chamber without any catalyst, producing water as a byproduct.

Example 15

In this example, syngas is added to the combustion chamber without any nitrogen gas (to prevent the production of $NH_3$ and $HNO_3$) to produce methanol, ethanol, and other higher alcohols and dimethyl ether.

Example 16

In this example, variations of oxygen and hydrogen are used to produce cyclohexane, aromatics, polyesters, nitrocellulose, ammonian picrate, tri-nitro toluene, nitrobenzene, silver nitrate, and isocyanate, derived from $HNO_3$. The choice and amounts of chemical precursor determine the product.

Example 17

In this example, the ethylene, propylene, and styrene can be added to the combustion chamber for the respective polymerization of ethylene to polyethylene, propylene to polypropylene, and styrene to polystyrene or acrylonitrile and polyamides, epoxies, and polyvinylchloride.

Example 18

In this example, synthetic fibers including acrylics, nylon, olefins, polyester, acetate, and rayon are produced.

Example 19

In this example, synthetic rubber products are produced (e.g., styrene-butadiene, polybutadiene, ethylene-propylene, nitrile, and polychloraphene) by repeated subjecting the precursors to cyclic heat/pressure in the combustion chamber.

Example 20

In this example, the combustion chamber is used to calcify lime. The heat and pressure alone calcifies lime during combustion in the presence of water vapor accompanying the hydrogen and oxygen.

Example 21

In this example, the combustion chamber is used to produce titanium oxide ($TiO_2$) from $TiCl_4$ in the presence of oxygen.

Example 22

In this example, sugar (e.g., 50% glucose and 40% fructose) is introduced to the combustion chamber to produce glucose products.

Example 23

In this example, the combustion chamber is used for the vulcanization in free-radical polymerization of 1,3 butadiene, and for the free radical polymerization of dienes.

Example 24

In these examples, the combustion chamber is used for the reactions shown by the following equations:

Acetic anhydride: $CH_3COH + H_2O \rightarrow CH_2CO \rightarrow CH_3CO_2COCH_3$ Hydrogen cyanide: $2CH_4 + 2NH_3 + 3O_2 \rightarrow 2HCN + 6H_2O$ Or Hydrogen cyanide: $CH_2CHCH_3 + 2NH_3 + 3O_2 \rightarrow 2CH_2CHCN + 6H_2O + H_2$ Analine: $NH_3 + C_6H_5NH_2 \rightarrow C_6H_5NH_3$ (in the presence of excess hydrogen and a catalyst)

Propylene Glycol: $CH_3CHOCH_2 + H_2O \rightarrow CH_3CH(OH)_2$

Diethylene Glycol: $CH_2OCH_2 + H_2O \rightarrow HO(CH_2)_2OH + HO(CH_2)_2OCH_2CH_2OH$ Nonene: $C_9H_2O \rightarrow C_9H_{18} + H_2$ (in the presence of a catalyst)

$2CH_3OH + O_2 \rightarrow CH_2O + 2H_2O$

Or

Formaldehyde: $CH_3OH \rightarrow CH_2O + H_2$

The invention claimed is:

1. A chemical production system comprising:
   a pulse jet combustion chamber having intake ports for entry of a gas mixture, and an igniter to ignite the gas mixture in the combustion chamber;
   a nozzle to restrict exit of the ignited gas mixture from the combustion chamber; and
   an expansion chamber to cool the ignited gas with a cooling agent, the expansion chamber having an exhaust where the cooled gas exits the expansion chamber, wherein the gas mixture is selected as a precursor to produce a chemical compound product in the expansion chamber.

2. The system of claim 1, wherein the combustion chamber reacts the gas mixture with at least oxygen and hydrogen at high temperature and high pressure.

3. The system of claim 1, wherein the combustion chamber reacts the gas mixture with at least oxygen, nitrogen, and hydrogen at high temperature and high pressure.

4. The system of claim 1 wherein the gas mixture includes a nitrogen source, a hydrogen source, and an oxygen source, and wherein the chemical compound product is nitrogen-based.

5. The system of claim 1, wherein the gas mixture includes carbon dioxide, and wherein the chemical compound product is methane and other higher order hydrocarbons, and wherein admitted materials further comprise liquids and gases including alkanes to produce polyethylene and used in chemical production under high pressure.

6. The system of claim 1, wherein the chemical compound product includes both gas and aqueous solution.

7. The system of claim 1, further comprising a catalyst in the combustion chamber.

8. The system of claim 1, wherein pollutants are admitted to the combustion chamber to render the pollutants inert following reaction in the combustion chamber.

9. The system of claim 1, wherein the combustion chamber is used to reform natural gas.

10. A method comprising:
    igniting a gas mixture from a hydrogen pulse jet combustion chamber;
    restricting exit of the ignited gas mixture from the combustion chamber to increase temperature and pressure;
    cooling the ignited gas in an expansion chamber; and
    collecting a chemical compound product from the expansion chamber.

11. The method of claim 10, further comprising forming a catalyst in the combustion chamber during reaction of the gas mixture.

12. The method of claim 10, further comprising steam reformation of any hydrocarbon into hydrogen with residual including carbon, CO, $CO_2$ and other hydrocarbons.

13. The method of claim 10, further comprising reformation of coal and petroleum into hydrogen and residual atomized solid or liquid.

14. The method of claim 13, wherein the residual is separated and removed from the hydrogen.

15. The method of claim 14, wherein the residual is used as in asphalt or other building material.

16. The method of claim 10, further comprising admitting to the combustion chamber, pollutants from power production or industrial chemical production, and rendering the pollutants inert following reaction in the combustion chamber.

17. The method of claim 10, further comprising admitting vapor or mist to the combustion chamber to modify combustion.

18. The method of claim 10, further comprising admitting fine ground coal to the combustion chamber to release residue.

19. The method of claim 10, further comprising reforming natural gas in the combustion chamber.

20. A method comprising:
   igniting a gas mixture in a combustion chamber;
   admitting vapor or mist to the combustion chamber to modify combustion product;
   restricting exit of the ignited gas mixture from the combustion chamber to increase pressure; and
   collecting a chemical compound product from the expansion chamber.

\* \* \* \* \*